(12) United States Patent
Tavernier et al.

(10) Patent No.: US 7,423,113 B2
(45) Date of Patent: Sep. 9, 2008

(54) LEPTIN ANTAGONIST

(75) Inventors: Jan Tavernier, Balegem (BE); Frank Peelman, Gentbrugge (BE)

(73) Assignees: VIB vzw, Zwijnaarde (BE); Universiteit Gent, Ghent (BE)

(*) Notice: Subject to any disclaimer, the term of this patent is extended or adjusted under 35 U.S.C. 154(b) by 413 days.

(21) Appl. No.: 10/926,798

(22) Filed: Aug. 25, 2004

(65) Prior Publication Data
US 2006/0046959 A1 Mar. 2, 2006

(51) Int. Cl.
*C07K 4/00* (2006.01)
(52) U.S. Cl. .................. 530/300; 530/326; 514/12
(58) Field of Classification Search ............ None
See application file for complete search history.

(56) References Cited

U.S. PATENT DOCUMENTS 5,972,621 A 10/1999 Tartaglia et al.

FOREIGN PATENT DOCUMENTS

| WO | WO 97/00319 | 1/1997 |
|---|---|---|
| WO | WO 97/20933 | 6/1997 |
| WO | WO 98/12224 | 3/1998 |
| WO | WO 99/40946 A2 | 8/1999 |
| WO | WO 02/40543 A1 | 5/2002 |
| WO | WO 02/062833 A2 | 8/2002 |

OTHER PUBLICATIONS

Rohner-Jearnrenaud et al., The New Eng. J. Med., 334: 324-325, 1996.*
Campfield et al., Science 280: 1383-1389, 1998.*
Grasso et al., Endocrinol. 138: 1413-1418, 1997.*
Verploegen et al., FEBS Letters 405, 237-240, 1997.*
Bjorbaek et al., The Role of SOCS-3 in Liptin Signaling and Leptin Resistance, The Journal of Biological Chemistry, Oct. 15, 1999, pp. 30059-65, vol. 274, No. 42.
Bonnefoy-Berard et al., Vav: Function and Regulation in Hematopoietic Cell Signaling, Stem Cells, 1996, pp. 250-68, vol. 14.
Gisselbrecht, The CIS/SOCS proteins: a family of cytokine-inducible regulators of signaling, European Cytokine Network, Dec. 1999, pp. 463-70, vol. 10, No. 4.
Lee et al., Abnormal splicing of the leptin receptor in diabetic mice, Nature, Feb. 15, 1996, pp. 632-635, vol. 379.
Mercer et al., Localization of leptin receptor mRNA and the long form splice variant (ob-Rb) in mouse hypothalamus and adjacent brain regions by in situ hybridization, FEBS Letters, 1996, pp. 113-16, vol. 387.
Tartaglia et al., Identification and Expression Cloning of a Leptin Receptor, OB-R, Cell, Dec. 29, 1995, pp. 1263-71, vol. 83.
Zabeau et al., The ins and outs of leptin receptor activations, FEBS Letters, 2003, pp. 45-50, vol. 546.

* cited by examiner

*Primary Examiner*—Robert S. Landsman
*Assistant Examiner*—Gyan Chandra
(74) *Attorney, Agent, or Firm*—TraskBritt (57) ABSTRACT

The present invention relates to an antagonist or inhibitor of leptin signaling via the leptin receptor. The leptin antagonist binds to the leptin receptor, but is unable to induce JAK-STAT signal transduction via the leptin receptor. By binding to the leptin receptor, the leptin antagonist impairs binding of leptin to the leptin receptor and blocks leptin signaling.

2 Claims, 4 Drawing Sheets

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: a leptin antagonist
<220> FEATURE:
<221> NAME/KEY: MISC_FEATURE
<222> LOCATION: (1)..(1)
<223> OTHER INFORMATION: X can be any amino acid, but not S
<220> FEATURE:
<221> NAME/KEY: MISC_FEATURE
<222> LOCATION: (2)..(2)
<223> OTHER INFORMATION: X can be any amino acid, but not T
<220> FEATURE:
<221> NAME/KEY: MISC_FEATURE
<222> LOCATION: (9)..(9)
<223> OTHER INFORMATION: X can be an R or W
<220> FEATURE:
<221> NAME/KEY: MISC_FEATURE
<222> LOCATION: (12)..(12)
<223> OTHER INFORMATION: X can be an G, A or R
<220> FEATURE:
<221> NAME/KEY: MISC_FEATURE
<222> LOCATION: (13)..(13)
<223> OTHER INFORMATION: X can be an S or A

<400> SEQUENCE: 1

Xaa Xaa Glu Val Val Ala Leu Ser Xaa Leu Gln Xaa Xaa Leu Gln Asp
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: a leptin antagonist
<220> FEATURE:
<221> NAME/KEY: MISC_FEATURE
<222> LOCATION: (2)..(2)
<223> OTHER INFORMATION: X can be any amino acid, but not T
<220> FEATURE:
<221> NAME/KEY: MISC_FEATURE
<222> LOCATION: (9)..(9)
<223> OTHER INFORMATION: X can be an R or W
<220> FEATURE:
<221> NAME/KEY: MISC_FEATURE
<222> LOCATION: (12)..(12)
<223> OTHER INFORMATION: X can be an G, A or R
<220> FEATURE:
<221> NAME/KEY: MISC_FEATURE
<222> LOCATION: (13)..(13)
<223> OTHER INFORMATION: X can be an S or A
```

-continued

<400> SEQUENCE: 2

Ala Xaa Glu Val Val Ala Leu Ser Xaa Leu Gln Xaa Xaa Leu Gln Asp
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: a leptin antagonist
<220> FEATURE:
<221> NAME/KEY: MISC_FEATURE
<222> LOCATION: (1)..(1)
<223> OTHER INFORMATION: X can be any amino acid, but not S
<220> FEATURE:
<221> NAME/KEY: MISC_FEATURE
<222> LOCATION: (9)..(9)
<223> OTHER INFORMATION: X can be an R or W
<220> FEATURE:
<221> NAME/KEY: MISC_FEATURE
<222> LOCATION: (12)..(12)
<223> OTHER INFORMATION: X can be an G, A or R
<220> FEATURE:
<221> NAME/KEY: MISC_FEATURE
<222> LOCATION: (13)..(13)
<223> OTHER INFORMATION: X can be an S or A

<400> SEQUENCE: 3

Xaa Ala Glu Val Val Ala Leu Ser Xaa Leu Gln Xaa Xaa Leu Gln Asp
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: a leptin antagonist
<220> FEATURE:
<221> NAME/KEY: MISC_FEATURE
<222> LOCATION: (9)..(9)
<223> OTHER INFORMATION: X can be an R or W
<220> FEATURE:
<221> NAME/KEY: MISC_FEATURE
<222> LOCATION: (12)..(12)
<223> OTHER INFORMATION: X can be an G, A or R
<220> FEATURE:
<221> NAME/KEY: MISC_FEATURE
<222> LOCATION: (13)..(13)
<223> OTHER INFORMATION: X can be an S or A

<400> SEQUENCE: 4

Ala Ala Glu Val Val Ala Leu Ser Xaa Leu Gln Xaa Xaa Leu Gln Asp
1               5                   10                  15

<210> SEQ ID NO 5
<211> LENGTH: 146
<212> TYPE: PRT
<213> ORGANISM: Artificial Sequence
<220> FEATURE:
<223> OTHER INFORMATION: a leptin antagonist
<220> FEATURE:
<221> NAME/KEY: MISC_FEATURE
<222> LOCATION: (120)..(120)
<223> OTHER INFORMATION: X can be any amino acid, but not S
<220> FEATURE:
<221> NAME/KEY: MISC_FEATURE
<222> LOCATION: (121)..(121)
<223> OTHER INFORMATION: X can be any amino acid, but not T

<400> SEQUENCE: 5

Val Pro Ile Gln Lys Val Gln Asp Asp Thr Lys Thr Leu Ile Lys Thr

```
                1               5                   10                  15
Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Xaa Xaa Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 6
<211> LENGTH: 28
<212> TYPE: DNA
<213> ORGANISM: Artificial Sequence
<220> FEATURE:
<223> OTHER INFORMATION: forward oligomeric primer used in example 2

<400> SEQUENCE: 6
gcgtccggaa tccagaaagt ccaggatg                                          28

<210> SEQ ID NO 7
<211> LENGTH: 31
<212> TYPE: DNA
<213> ORGANISM: Artificial Sequence
<220> FEATURE:
<223> OTHER INFORMATION: reverse primer used in example 2

<400> SEQUENCE: 7
cgctctagat tagcattcag ggctaacatc c                                      31

<210> SEQ ID NO 8
<211> LENGTH: 178
<212> TYPE: PRT
<213> ORGANISM: Mus musculus
<220> FEATURE:
<221> NAME/KEY: MISC_FEATURE
<223> OTHER INFORMATION: SlgK-HA-mouse leptin

<400> SEQUENCE: 8

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Gly
            20                  25                  30

Ser Gly Ile Gln Lys Val Gln Asp Asp Thr Lys Thr Leu Ile Lys Thr
        35                  40                  45

Ile Val Thr Arg Ile Asn Asp Ile Ser His Thr Gln Ser Val Ser Ala
    50                  55                  60

Lys Gln Arg Val Thr Gly Leu Asp Phe Ile Pro Gly Leu His Pro Ile
65                  70                  75                  80
```

```
Leu Ser Leu Ser Lys Met Asp Gln Thr Leu Ala Val Tyr Gln Gln Val
                85                  90                  95
Leu Thr Ser Leu Pro Ser Gln Asn Val Leu Gln Ile Ala Asn Asp Leu
            100                 105                 110
Glu Asn Leu Arg Asp Leu Leu His Leu Leu Ala Phe Ser Lys Ser Cys
        115                 120                 125
Ser Leu Pro Gln Thr Ser Gly Leu Gln Lys Pro Glu Ser Leu Asp Gly
    130                 135                 140
Val Leu Glu Ala Ser Leu Tyr Ser Thr Glu Val Val Ala Leu Ser Arg
145                 150                 155                 160
Leu Gln Gly Ser Leu Gln Asp Ile Leu Gln Gln Leu Asp Val Ser Pro
                165                 170                 175
Glu Cys

<210> SEQ ID NO 9
<211> LENGTH: 40
<212> TYPE: DNA
<213> ORGANISM: Artificial Sequence
<220> FEATURE:
<223> OTHER INFORMATION: primer O-1701

<400> SEQUENCE: 9
caagaccatt gtcaccaaca ttaatgacat ttcacacacg                    40

<210> SEQ ID NO 10
<211> LENGTH: 40
<212> TYPE: DNA
<213> ORGANISM: Artificial Sequence
<220> FEATURE:
<223> OTHER INFORMATION: primer O-1702

<400> SEQUENCE: 10
cgtgtgtgaa atgtcattaa tgttggtgac aatggtcttg                    40

<210> SEQ ID NO 11
<211> LENGTH: 37
<212> TYPE: DNA
<213> ORGANISM: Artificial Sequence
<220> FEATURE:
<223> OTHER INFORMATION: primer O-1821

<400> SEQUENCE: 11
ggaagcctca ctctacgccg cggaggtggt ggctttg                       37

<210> SEQ ID NO 12
<211> LENGTH: 37
<212> TYPE: DNA
<213> ORGANISM: Artificial Sequence
<220> FEATURE:
<223> OTHER INFORMATION: primer O-1822

<400> SEQUENCE: 12
caaagccacc acctccgcgg cgtagagtga ggcttcc                       37

<210> SEQ ID NO 13
<211> LENGTH: 43
<212> TYPE: DNA
<213> ORGANISM: Artificial Sequence
<220> FEATURE:
<223> OTHER INFORMATION: primer O-1769

<400> SEQUENCE: 13
ggatgacacc aaaaccaaca tcaagacaat tgtcaccagg atc                43
```

<210> SEQ ID NO 14
<211> LENGTH: 43
<212> TYPE: DNA
<213> ORGANISM: Artificial Sequence
<220> FEATURE:
<223> OTHER INFORMATION: primer O-1770

<400> SEQUENCE: 14
gatcctggtg acaattgtct tgatgttggt tttggtgtca tcc          43

<210> SEQ ID NO 15
<211> LENGTH: 178
<212> TYPE: PRT
<213> ORGANISM: Artificial Sequence
<220> FEATURE:
<223> OTHER INFORMATION: mouse leptin mutant R20N

<400> SEQUENCE: 15

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Gly
            20                  25                  30

Ser Gly Ile Gln Lys Val Gln Asp Asp Thr Lys Thr Leu Ile Lys Thr
        35                  40                  45

Ile Val Thr Asn Ile Asn Asp Ile Ser His Thr Gln Ser Val Ser Ala
    50                  55                  60

Lys Gln Arg Val Thr Gly Leu Asp Phe Ile Pro Gly Leu His Pro Ile
65                  70                  75                  80

Leu Ser Leu Ser Lys Met Asp Gln Thr Leu Ala Val Tyr Gln Gln Val
                85                  90                  95

Leu Thr Ser Leu Pro Ser Gln Asn Val Leu Gln Ile Ala Asn Asp Leu
            100                 105                 110

Glu Asn Leu Arg Asp Leu Leu His Leu Leu Ala Phe Ser Lys Ser Cys
        115                 120                 125

Ser Leu Pro Gln Thr Ser Gly Leu Gln Lys Pro Glu Ser Leu Asp Gly
    130                 135                 140

Val Leu Glu Ala Ser Leu Tyr Ser Thr Glu Val Val Ala Leu Ser Arg
145                 150                 155                 160

Leu Gln Gly Ser Leu Gln Asp Ile Leu Gln Gln Leu Asp Val Ser Pro
                165                 170                 175

Glu Cys
```

<210> SEQ ID NO 16
<211> LENGTH: 178
<212> TYPE: PRT
<213> ORGANISM: Artificial Sequence
<220> FEATURE:
<223> OTHER INFORMATION: mouse leptin mutant L13N

<400> SEQUENCE: 16

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Gly
            20                  25                  30

Ser Gly Ile Gln Lys Val Gln Asp Asp Thr Lys Thr Asn Ile Lys Thr
        35                  40                  45

Ile Val Thr Arg Ile Asn Asp Ile Ser His Thr Gln Ser Val Ser Ala
    50                  55                  60
```

```
Lys Gln Arg Val Thr Gly Leu Asp Phe Ile Pro Gly Leu His Pro Ile
 65                  70                  75                  80

Leu Ser Leu Ser Lys Met Asp Gln Thr Leu Ala Val Tyr Gln Gln Val
                 85                  90                  95

Leu Thr Ser Leu Pro Ser Gln Asn Val Leu Gln Ile Ala Asn Asp Leu
                100                 105                 110

Glu Asn Leu Arg Asp Leu Leu His Leu Leu Ala Phe Ser Lys Ser Cys
            115                 120                 125

Ser Leu Pro Gln Thr Ser Gly Leu Gln Lys Pro Glu Ser Leu Asp Gly
        130                 135                 140

Val Leu Glu Ala Ser Leu Tyr Ser Thr Glu Val Val Ala Leu Ser Arg
145                 150                 155                 160

Leu Gln Gly Ser Leu Gln Asp Ile Leu Gln Gln Leu Asp Val Ser Pro
                165                 170                 175

Glu Cys

<210> SEQ ID NO 17
<211> LENGTH: 178
<212> TYPE: PRT
<213> ORGANISM: Artificial Sequence
<220> FEATURE:
<223> OTHER INFORMATION: mouse leptin mutant S120AT121A

<400> SEQUENCE: 17

Met Glu Thr Asp Thr Leu Leu Trp Val Leu Leu Trp Val Pro
  1               5                  10                  15

Gly Ser Thr Gly Asp Tyr Pro Tyr Asp Val Pro Asp Tyr Ala Gly Gly
                 20                  25                  30

Ser Gly Ile Gln Lys Val Gln Asp Asp Thr Lys Thr Leu Ile Lys Thr
             35                  40                  45

Ile Val Thr Arg Ile Asn Asp Ile Ser His Thr Gln Ser Val Ser Ala
         50                  55                  60

Lys Gln Arg Val Thr Gly Leu Asp Phe Ile Pro Gly Leu His Pro Ile
 65                  70                  75                  80

Leu Ser Leu Ser Lys Met Asp Gln Thr Leu Ala Val Tyr Gln Gln Val
                 85                  90                  95

Leu Thr Ser Leu Pro Ser Gln Asn Val Leu Gln Ile Ala Asn Asp Leu
                100                 105                 110

Glu Asn Leu Arg Asp Leu Leu His Leu Leu Ala Phe Ser Lys Ser Cys
            115                 120                 125

Ser Leu Pro Gln Thr Ser Gly Leu Gln Lys Pro Glu Ser Leu Asp Gly
        130                 135                 140

Val Leu Glu Ala Ser Leu Tyr Ala Ala Glu Val Val Ala Leu Ser Arg
145                 150                 155                 160

Leu Gln Gly Ser Leu Gln Asp Ile Leu Gln Gln Leu Asp Val Ser Pro
                165                 170                 175

Glu Cys
```

LEPTIN ANTAGONIST

TECHNICAL FIELD

The present invention relates generally to biotechnology, particularly to an antagonist or inhibitor of leptin signaling via the leptin receptor. The leptin antagonist binds to the leptin receptor, but is unable to induce JAK-STAT signal transduction via the leptin receptor. By binding to the leptin receptor, the leptin antagonist impairs binding of leptin to the leptin receptor and blocks leptin signaling.

BACKGROUND

After cleavage of its 21 amino acids signal peptide (Cohen et al., 1996), mature human leptin is secreted as a 146 amino acid protein, with a typical type II interleukin structure, consisting of a bundle of 4 helices (helix 1-4), with an up-up-down-down topology (Zhang et al., 1997). Leptin is secreted into the bloodstream primarily by adipocytes, and blood concentrations of leptin correlate with white adipose tissue mass. Leptin acts as an energy homeostasis hormone, regulating energy expenditure and food intake.

Leptin does so by binding to the leptin receptor in certain areas in the hypothalamus, which leads to phosphorylation of STAT molecules that subsequently migrate to the cell nucleus and induce transcription of different genes.

In addition to its adipostatic function, leptin has many other functions: it can induce proliferation, differentiation and functional activation of hemopoietic cells (Gainsford et al., 1996), and induces angiogenesis (Sierra-Honigmann et al., 1998).

Leptin also interacts with the immune and inflammatory responses (Loffreda et al., 1998).

Leptin levels are acutely increased by inflammatory stimuli and by pro-inflammatory cytokines TNF-α and IL-1 (Grunfeld et al., 1996). Leptin itself regulates the production of several cytokines in vitro, regulates the T helper (Th1/Th2) balance, and can up-regulate inflammatory responses (Loffreda et al., 1998; Faggioni et al., 1998; Lord et al., 1998).

The human leptin receptor is expressed at the cell surface of many different tissues. At least six different splice variants of the human leptin receptor were found at present. The longest isoform of the human leptin receptor consists of 1162 amino acids, with an extracellular region between residues 1 and 840, a transmembrane region between residues 841 and 863 and an intracellular region between residues 864 and 1162.

The extracellular part of the human leptin receptor contains at least 7 structural domains (Fong et al., 1998).

Domain 1 (residue 62-178) and 2 (residue 235-328) have a fibronectin type III fold and together form a cytokine receptor module (CRM), named CRM1.

Domain 3 (residue 329-427) has an Immunoglobulin type fold.

Domain 4 (residue 428-535) and 5 (residue 536-635) also have a fibronectine type III fold and together form a second cytokine receptor module (CRM), named CRM2.

Domains 6 and 7 have a fibronectin type III domain structure.

Like all members of the class I cytokine receptor family, the leptin receptor has no intrinsic kinase activity, and uses a cytoplasmic associated Janus kinase (JAK2 in case of the leptin receptor) for intracellular signaling (Ghilardi et al., 1997). In a generally accepted model, leptin binding leads to formation of a receptor complex, allowing activation of JAK2 by cross-phosphorylation. Activated JAK2 then rapidly phosphorylates several tyrosine residues in the cytosolic domain of the leptin receptor. These phosphorylated tyrosine residues provide docking sites for SH2 containing signaling molecules. In the mouse leptin receptor, tyrosine 1138 serves as a binding site for signal transducer and activator of transcription 3 (STAT3) (Baumann et al., 1996). STAT3 itself is a substrate for JAK2 and dimerizes upon phosphorylation, translocates to the nucleus and modulates transcription of target genes.

The leptin receptor shows the highest sequence similarity with the cytokine receptors of the IL-6 family and with the Granulocyte Colony-Stimulating Factor (G-CSF) Receptor. FSSP (Holm and Sander, 1997) structural similarity searches reveal that leptin shows the highest structural similarity with the cytokines of the IL-6 family and G-CSF, and to a lesser extent with other long chain cytokines, such as the growth hormone and placental lactogen. The crystal structure of the Kaposi's sarcoma-associated herpes virus IL-6 (vIL6, viral IL-6) in a 2:2 complex with the three N-terminal extracellular domains of human gp130 reveals two binding sites, binding site II and binding site III, for interaction between vIL6 and gp130 (Chow et al., 2001). Binding site II, consisting of residues in helices 1 and 3 of vIL6, interacts with the cytokine receptor module (CRM) of gp130. Binding site III in vIL6 consists of residues in the N-terminus of helix 4, in the loop connecting helix 3 and 4 and in the loop connecting helix 1 and 2, and interacts with the Immunoglobulin-like domain of gp130. Corresponding site II and III residues were identified in other members of the IL-6 family of cytokines by site directed mutagenesis: human IL-6, human IL-11, Leukemia inhibitory factor (LIF), oncostatin M (OSM) and Ciliary neurotrophic factor (CNTF) (Kalai et al., 1997; Savino et al., 1993; DiMarco et al., 1996; Hudson et al., 1996; Inoue et al., 1995; Barton et al., 1999; Bravo and Heath, 2000).

Figure 1:
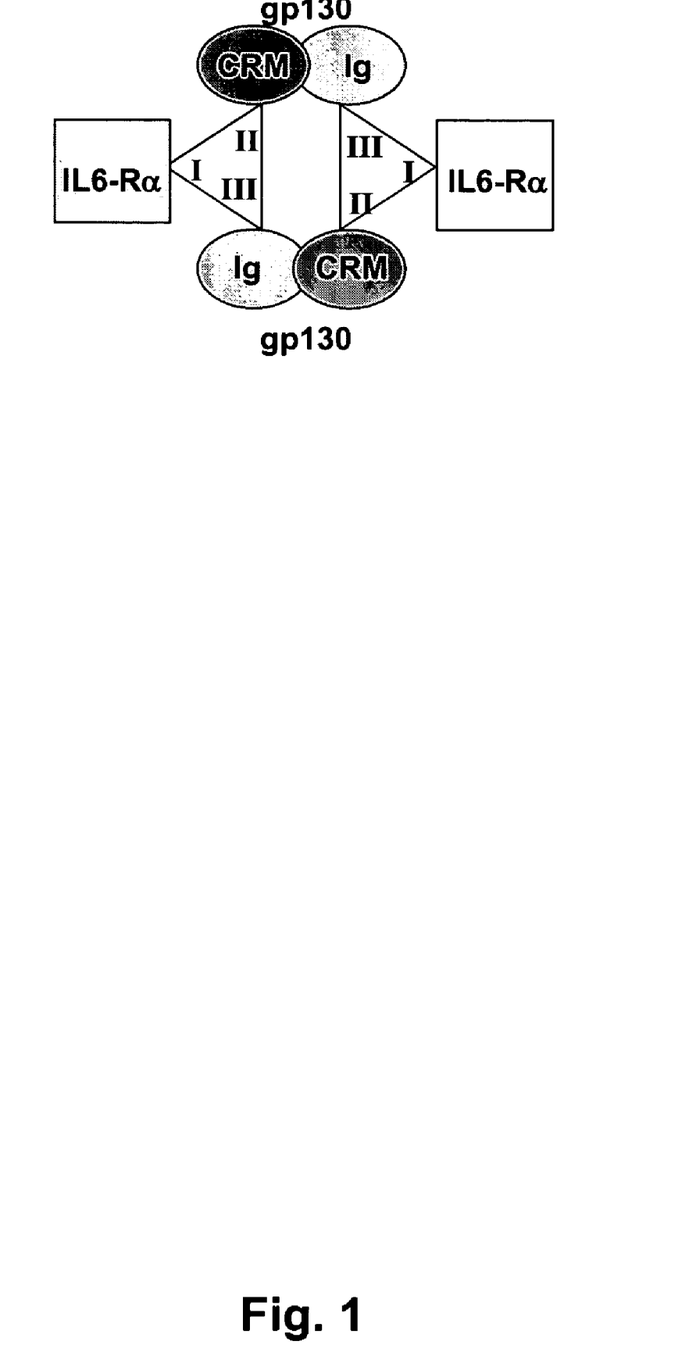
FIG. 1: composition of the 2:2:2 IL-6:gp130:IL-6Rα complex.
Figure 2:
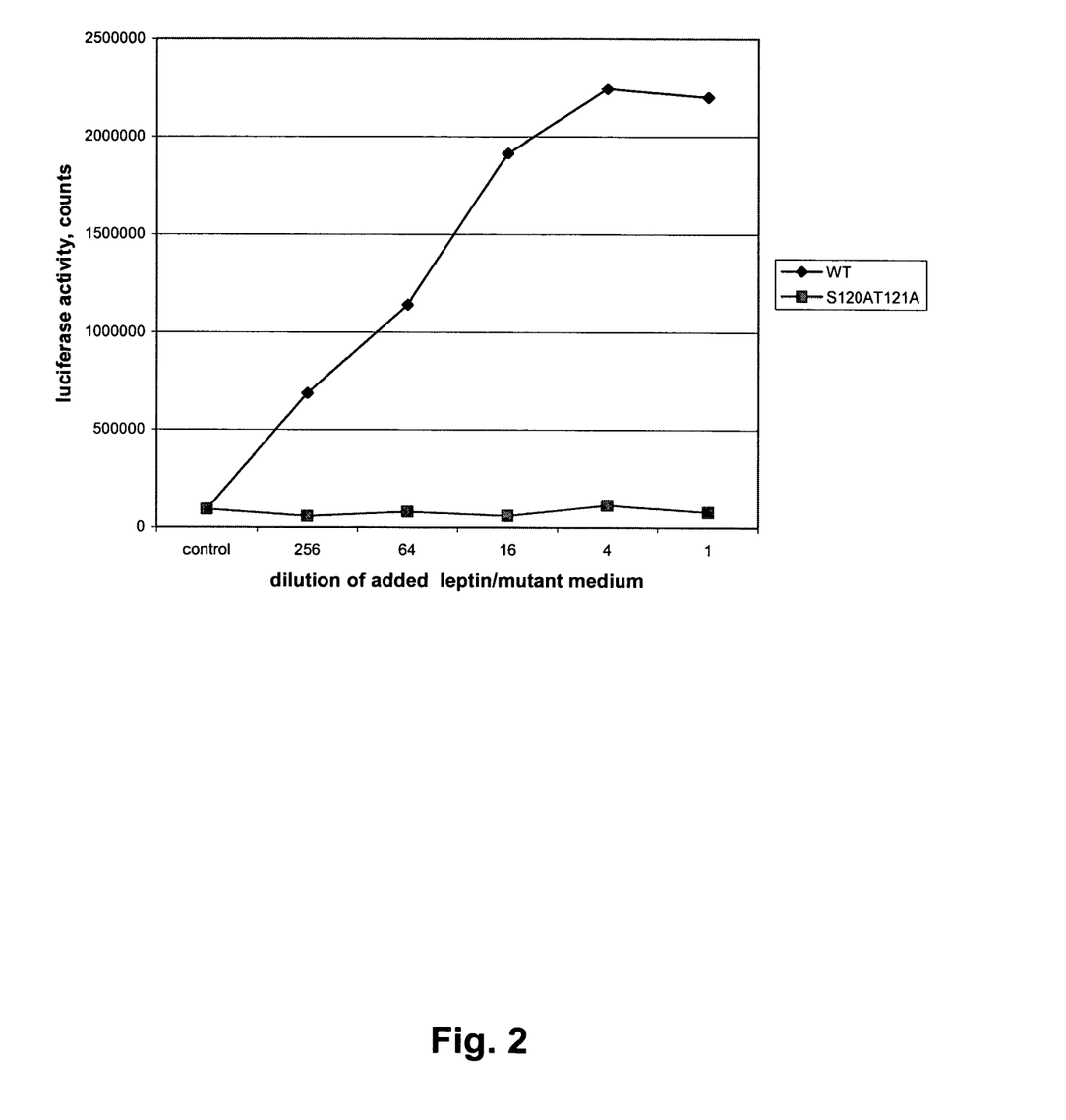
FIG. 2: Activation of luciferase as reporter by WT leptin and the S120AT121A mutant.

IL-6 contains a third binding site, binding site I, for interaction with the IL-6 α receptor. Human IL-6 forms a hexameric 2:2:2 complex with its gp130 and IL-6 α receptor chains: each IL-6 molecule binds two gp130 molecules by its site II and III binding sites, and one IL-6 receptor α subunit (IL-6Rα) by its binding site I (FIG. 1) (Boulanger et al., 2003).

Activation of the leptin receptor by binding of leptin plays a role in several physiological processes. Several variant and mutant forms of leptin have been described, that can be used in different applications. PCT International Patent Publication No. WO02062833 describes modified leptin polypeptides that are substantially non-immunogenic or less immunogenic than any non-modified counterpart when used in vivo. These polypeptides can be administered to humans of therapeutic use. PCT International Patent Publication No. WO9700319 discloses chimeric leptin polypeptides comprising leptin or a mutant or variant thereof fused to a human immunoglobulin domain. These chimeric derivatives have prolonged clearing rates and may be useful in the treatment or prophylaxis of obesity, or diseases and conditions associated with obesity such as atherosclerosis, hypertension and type II diabetes. PCT International Patent Publication No. WO9720933 discloses mutational variants of the mammalian leptin. These molecules can serve as agonist or antagonist of the wild-type leptin; their capacity to induce the signaling pathway upon binding of the receptor varies for the different muteins. PCT International Patent Publication No. WO9812224 describe the use of fragments, derived from leptin, as leptin antagonist, especially for treating type II diabetes.

A need remains for a leptin mutant that is able to bind to the receptor, with a similar or higher affinity as the wild-type leptin, but without remaining signaling activity. Such leptin mutant would be a powerful antagonist and can be used to treat leptin-mediated diseases.

DISCLOSURE OF THE INVENTION

Surprisingly, we found that leptin, similar to IL-6 and G-CSF, has a binding site II and III, which are both involved in binding to the leptin receptor. As is the case for G-CSF and for members of the IL-6 family, binding site II consists of residues in helix 1 (residues 4-26) and 3 (residues 71-93). These residues are involved in high affinity binding to the CRM2 module of the leptin receptor, and mutations in binding site II of mouse leptin decrease or even abolish the affinity of the mutant leptin to the mouse leptin receptor. Due to the decreased binding, these mutants show a decreased induction of JAK-STAT signaling via the leptin receptor.

Binding site III consists of residues in the loop connecting helix 1 and 2 (residues 27-50) and of residues at the N-terminus of helix 4 (residues 105-122). Mutations in this binding site do not -affect the high affinity binding to the leptin receptor or to the CRM2 module, but still show a decreased induction of JAK-STAT signaling via the leptin receptor. The S120AT121A mutation in mouse leptin binding site III is unable to induce any JAK-STAT reporter activity via the mouse leptin receptor, although the binding affinity of this mutant for the leptin receptor or for CRM2 of the mouse leptin receptor is similar to that of wild-type leptin.

Even more surprisingly, we found that the S120AT121A mouse leptin mutant can inhibit the binding of wild-type leptin to its receptor, and can inhibit the JAK-STAT signal induced by wild-type leptin. This is because the S120AT121A leptin mutant shows an intact binding site II, and avidly binds to CRM2 of the leptin receptor, thus competing for binding of wild-type leptin. Unlike wild-type leptin, however, binding of the S120AT121 A mutant does not induce JAK-STAT signaling.

In one aspect of the invention, a leptin antagonist of polypeptidic nature comprises SEQ ID NO:1. Preferably, the leptin antagonist is comprising SEQ ID NO:2 or SEQ ID NO:3, even more preferably, the leptin antagonist is comprising SEQ ID NO:4. Preferably, the leptin antagonist is binding to the leptin receptor, without inducing the signaling pathway. A preferred embodiment is a leptin antagonist according to the invention, capable of binding the leptin receptor without inducing the signaling pathway, whereby the antagonist is mutated in amino acid 120 and/or 121 of SEQ ID NO:5. Preferably, amino acid 120 or amino acid 121 are mutated into an alanine. Even more preferably, both amino acids are changed into alanine.

Another preferred embodiment is a leptin antagonist of polypeptidic nature, capable of binding the leptin receptor without inducing the signaling pathway, comprising SEQ ID NO:5 or a functional fragment or variant thereof. A functional fragment as used here is a fragment that still can bind to the leptin receptor. A variant as used here implies that besides the amino acids 120 and 121, other amino acids may differ from the wild-type human leptin sequence. Chemical modifications of the antagonist are also considered as variants. Chemical modifications of polypeptides are known to the person skilled in the art, and include but are not limited to natural occurring modifications such as glycosylation, phosphorylation, ubiquitinilation and artificial modifications such as PEGylation. Preferably, the chemical modification is increasing the half-life time of the polypeptide. Even more preferably, the chemical modification is PEGylation. Preferably, the variant is at least 70% identical to the wild-type sequence, more preferably, it is at least 80% identical to the wild-type sequence, even more preferably, it is at least 90% identical to the wild-type sequence, most preferable, it is 95% identical to the wild-type sequence. The functional fragment can be used as such, or it may be fused to another polypeptide. In the latter case, the fusion polypeptide has, preferably, an increased antagonistic capacity. Possible fusion partners are, as a non-limiting example, polypeptides that increase the half-life time of the polypeptide in vivo. Such polypeptides are disclosed, amongst others, in PCT International Patent Publication No. WO9700319. Alternatively, the fusion partner may capture leptin itself, thereby increasing the antagonistic activity. Polypeptides that capture leptin are, as a non-limiting example, leptin antibodies, preferably single chain antibodies, or a domain of the leptin receptor that is binding leptin.

A preferred fusion partner for the antagonist it the immunoglobulin type fold domain of the leptin receptor. This domain is involved in leptin dependent oligomerization of the leptin receptor, and subsequent signaling. Fusion of this domain to the antagonist will therefore give an increased antagonistic affect, by disturbing the leptin-induced oligomerization of the receptor.

Another aspect of the invention is the use of a leptin antagonist according to the invention to treat T-cell-mediated immune and/or autoimmune diseases. Indeed, leptin enhances T cell-mediated immune responses, by signaling through the long form of the leptin receptor on CD4+ T lymphocytes (Lord et al., 1998). Leptin shifts the T-cell responses towards a Th1 type, with increased secretion of pro-inflammatory cytokines IL-2 and interferon-γ, and decreased IL-4 production. A leptin antagonist can therefore be used for modifying/attenuating the T-cell immune responses, with use as a drug for the treatment of T-cell-mediated (auto-) immune diseases.

Still another aspect of the invention is the use of an antagonist according to the invention to treat intestinal inflammation diseases. Preferably, the intestinal inflammation diseases are selected from the group consisting of Crohn's disease, ulcerative colitis and intestinal infectious diseases. In experimental mouse model systems, where chronic and acute colitis is induced by dextran sulfate sodium or trinitrobenzene sulfonic acid, leptin deficient mice (ob/ob mice), show a 72% reduction of colitis severity and a similar decrease of pro-inflammatory cytokines in the intestine, compared to wild-type mice (Siegmund et al., 2002). Administration of leptin in the leptin deficient mice abolishes the resistance against experimentally induced colitis (Siegmund et al., 2002). Administration of *Clostridium difficile* toxin A induces severe colitis in mice. Leptin deficient (ob/ob) mice, as well as leptin receptor deficient (db/db) mice are partially protected against the toxin A-induced intestinal secretion and inflammation (Mykoniatis et al., 2003). In ob/ob, but not in db/db mice, leptin administration reverses the protection against toxin A-induced intestinal secretion and inflammation (Mykoniatis et al., 2003). A leptin antagonist can therefore be used as a drug for treatment of intestinal inflammation diseases, such as Crohn's disease, ulcerative colitis and intestinal infectious diseases.

In case of intestinal inflammation diseases, a preferred delivery method for the leptin antagonist according to the invention is an in vivo delivery system, as described in WO9714806. Therefore, another aspect of the invention is a lactic acid bacterium, producing a leptin antagonist according to the invention. Preferably, the lactic acid bacterium is a *Lactobacillus*, even more preferably, the lactic acid bacterium is a *Lactococcus*.

A further aspect of the invention is the use of a leptin antagonist according to the invention to treat rheumatoid arthritis. Administration of methylated BSA in the knees of mice leads to the development of Antigen-induced arthritis. As compared to wild-type mice, leptin deficient (ob/ob) mice and leptin receptor deficient (db/db) mice develop less severe arthritis, with decreased IL-1β and TNF-α in the knee synovial fluid, decreased serum levels of anti-methylated BSA antibodies and a decreased antigen-specific T cell proliferative response (Busso et al., 2002). A leptin antagonist can therefore be used as a drug for treatment of rheumatoid arthritis.

Still another aspect of the invention is the use of a leptin antagonist according to the invention to treat multiple sclerosis. The clinical onset of experimental autoimmune encephalomyelitis (EAE), a mouse model for multiple sclerosis, in disease-susceptible C57BL/6J(H-2b) and SJL/J(H-2s) mice is preceded by an increase in serum leptin concentrations (Sanna et al., 2003). This increase is correlated with disease susceptibility. Acute starvation, which reduces serum leptin levels, delays disease onset and attenuates the EAE symptoms. Leptin-deficient C57BL/6J-ob/ob mice are resistant against EAE, while this resistance is abolished by administration of leptin (Matarese et al., 2001). These data strongly indicate that leptin is a required factor for development of EAE, and thus, probably for multiple sclerosis. A leptin antagonist can therefore be used as a drug for treatment of multiple sclerosis.

A further aspect of the invention is the use of a leptin antagonist of the invention to treat Type 1 diabetes. Type 1 diabetes is an autoimmune disease, in which the pancreatic β-cells are destroyed by inflammatory processes. In the non-obese diabetic (NOD) mouse, an animal model for type 1 diabetes, an increased serum level of leptin precedes the diabetes in susceptible females, while injection of leptin accelerates the autoimmune destruction of the pancreatic β-cells (Matarese et al., 2002). A leptin antagonist can be used as a drug for preventing/treating type 1 diabetes.

A further aspect of the invention is the use of a leptin antagonist according to the invention to prevent and/or treat diseases characterized by T-cell-mediated hepatotoxicity. Leptin deficient ob/ob mice are protected from T cell-mediated hepatitis, experimentally induced with ConA or *Pseudomonas aeruginosa* exotoxin A (Faggioni et al., 2000). Injection of leptin in the leptin deficient mice restores the hepatotoxicity of these compounds (Faggioni et al., 2000). A leptin antagonist can therefore be used for treatment and/or prevention of diseases characterized by T-cell-mediated hepatotoxicity.

Still another aspect of the invention is a pharmaceutical composition, comprising a leptin antagonist according to the invention, optionally with a pharmaceutical acceptable excipient. Suitable excipients are known to the person skilled in the art, and are inherently non-toxic and non-therapeutic. Excipients may be, as a non-limiting example, Ringer's solution, dextrose solution or Hank's solution. Non-aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

DETAILED DESCRIPTION OF THE INVENTION

The invention is further explained with the aid of the following illustrative examples.

EXAMPLES

Example 1

Detection of Binding Site II and III in Human and Mouse Leptin by Structural Superposition FSSP structural similarity searches reveal that leptin shows the highest structural similarity with the cytokines of the IL-6 family and G-CSF, and to a minor extent with other long chain cytokines, such as the growth hormone and placental lactogen.

The crystal structures of human leptin (1ax8), human CNTF (1cnt), human IL-6 (1a1u), bovine G-CSF(1bgc), vIL6 (1i1r), ovine placental lactogen (1f6f), murine LIF (11ki) and human OSM (1evs) were superposed, using the FSSP and Prosup algorithms. Human leptin residues overlapping with binding site II or III residues in the other cytokines were considered as possible binding site II or III residues in human leptin.

A homology model was built for murine leptin, by replacing non-identical residues in human leptin structure by the optimal rotamer of the corresponding residue in mouse leptin, followed by energy minimization, using moe and the charmm22 force field. Residues aligning with the possible binding site II or III residues in human leptin were considered as possible binding site II or III residues in human leptin. Solvent-exposed residues in the predicted binding site II and III were mutated in the pMET7-SIgK-HA-mLep expression vector, and the mutant leptin was expressed in COS-1 cells.

Example 2

Generation of the Mouse Leptin Expression Vector pMet7-SIgK-HA-mouse Leptin

The pCDM8 mleptin-AP vector is containing the mouse leptin sequence, followed by the human alkaline phosphatase sequence. The wild-type (wt) mouse leptin sequence was isolated from this vector by PCR, using the 5' forward oligomeric primer 5'-GCGTCCGGAATCCAGAAAGTCCAG-GATG-3' (SEQ ID NO:6), containing a BspEI restriction site, and the 3' reverse primer 5'-CGCTCTAGATTAGCAT-TCAGGGCTAACATCC-3' (SEQ ID NO:7), containing an XbaI restriction site. The pMET7-SIgK-HA-LRlo plasmid contains the SIgK signal peptide, followed by the HA tag sequence and the mouse leptin receptor sequence. The leptin receptor sequence was excised from this vector, using the BspEI and XbaI restriction enzymes, and the mouse leptin sequence was ligated into this opened vector. The resulting vector, pMET7-SIgK-HA-mLep, allows the expression of a fusion protein, consisting of the SIgK signal peptide, followed by the HA-tag sequence, followed by a 4 amino acid GGSG linker, followed by amino acids 3 to 146 of mouse leptin. Upon expression in eukaryotic cells, the SIgK signal peptide is cleaved off and the HA-tagged protein is secreted in the medium.

Amino acid sequence (SEQ ID NO:8) of SIgK-HA-mouse leptin: the arrow indicates the predicted cleavage site of the SIgK signal peptide, the numbers above the sequence indicate the residue numbers in mouse leptin:

```
                          3                        28
                          |                        |
METDTLLLWVLLLWVPGSTGD YPYDVPDYA GGSG IQKVQDDTKTLIKTIVTRINDISHTQ
   SIgK signal peptide  ⇑  HA-tag    GGSG  mouse leptin
29                                                           88
|                                                            |
SVSAKQRVTGLDFIPGLHPILSLSKMDQTLAVYQQVLTSLPSQNVLQIANDLENLRDLLH
89                         120 121                       146
|                           |  |                          |
LLAFSKSCSLPQTSGLQKPESLDGVLEASLYSTEVVALSRLQGSLQDILQQLDVSPEC
```

Example 3

Generation of Mouse Leptin Mutants

The mouse leptin S120AT121A mutation was introduced in the pMET7-SIgK-HA-mLep by PCR using primers O-1821 and O-1822.

The mouse leptin R20N mutation was introduced in the pMET7-SIgK-HA-mLep by PCR using primers O-1701 and O-1702.

The mouse leptin L13N mutation was introduced in the pMET7-SIgK-HA-mLep by PCR using primers O-1769 and O-1770.

| Oligo | Specification | Sequence | |
|---|---|---|---|
| O-1701 | Mutation R20N in mouse leptin | CAAGACCATTGTCACCAACATTAATGACATTTC ACACACG | (SEQ ID NO:_) |
| O-1702 | Mutation R20N in mouse leptin | CGTGTGTGAAATGTCATTAATGTTGGTGACAAT GGTCTTG | (SEQ ID NO:_) |
| O-1821 | Mutation S120AT121A in mouse leptin | GGAAGCCTCACTCTACGCCGCGGAGGTGGTGGC TTTG | (SEQ ID NO:_) |
| O-1822 | Mutation S120AT121A in mouse leptin | CAAAGCCACCACCTCCGCGGCGTAGAGTGAGGC TTCC | (SEQ ID NO:_) |
| O-1769 | Mutation L13N in mouse leptin | GGATGACACCAAAACCAACATCAAGACAATTGT CACCAGGATC | (SEQ ID NO:_) |
| O-1770 | Mutation L13N in mouse leptin | GATCCTGGTGACAATTGTCTTGATGTTGGTTTT GGTGTCATCC | (SEQ ID NO:_) |

All mutations were introduced using the QuickChange method (Stratagene) according to the manufacturer's specifications.

Amino acid sequence (SEQ ID NO:15) of the mouse leptin mutants: vertical arrows indicate the position of the mutations, the numbers above the sequence indicate the residue numbers in mouse leptin:

1. R20N

```
                            3              20    28
                            |              |     |
METDTLLLWVLLLWVPGSTGD YPYDVPDYA GGSG IQKVQDDTKTLIKTIVTNINDISHTQ
                                                  ⇑
29                                                              88
|                                                               |
SVSAKQRVTGLDFIPGLHPILSLSKMDQTLAVYQQVLTSLPSQNVLQIANDLENLRDLLH
89                         120121               146
|                           ||                   |
LLAFSKSCSLPQTSGLQKPESLDGVLEASLYSTEVVALSRLQGSLQDILQQLDVSPEC
```

2. L13N

```
                            3         13       28
                            |         |        |
METDTLLLWVLLLWVPGSTGD YPYDVPDYA GGSG IQKVQDDTKTNIKTIVTRINDISHTQ
                                              ⇑
29                                                              88
|                                                               |
SVSAKQRVTGLDFIPGLHPILSLSKMDQTLAVYQQVLTSLPSQNVLQIANDLENLRDLLH
89                         120121               146
|                           ||                   |
LLAFSKSCSLPQTSGLQKPESLDGVLEASLYSTEVVALSRLQGSLQDILQQLDVSPEC
```

3. S120AT121A

```
                            3                   28
                            |                   |
METDTLLLWVLLLWVPGSTGD YPYDVPDYA GGSG IQKVQDDTKTLIKTIVTRINDISHTQ
29                                                              88
|                                                               |
SVSAKQRVTGLDFIPGLHPILSLSKMDQTLAVYQQVLTSLPSQNVLQIANDLENLRDLLH
89                         120121               146
|                           ||                   |
LLAFSKSCSLPQTSGLQKPESLDGVLEASLYAAEVVALSRLQGSLQDILQQLDVSPEC
                                 ⇑⇑
```

Example 4

Expression of the HA-tagged Mouse Leptin and HA-tagged Mouse Leptin Mutants in COS-1 Cells COS-1 cells were seeded at $4 \times 10^5$ cells/well in 6-well plates, and grown overnight.

The cells were then transfected using the polyethyleneimine (PEI) transfection method with the pMet7-SIgK-HA-mLep or the R20N, L13N or S120AT121A mutants in this vector.

The medium was replaced after 4 hours transfection, and cells were incubated overnight, after which the medium was replaced by 2 ml OPTI-MEM medium (Gibco-BRL). After another 72 hours, the OPTI-MEM medium containing the secreted HA-tagged leptin or HA-tagged leptin mutant was collected, and cells were removed by centrifugation.

Example 5

Purification of HA-tagged S120AT121A Mouse Leptin

COS-1 cells were seeded at $8 \times 10^6$ cells per 175 cm$^2$ flask in DMEM medium. Ten 175 cm$^2$ flasks were transfected with the S120AT121A pMET7-SIgK-HA-mLep mutant by transfection using polyethyleneimine. After 4 hours, the medium was replaced by fresh DMEM medium, and cells were grown overnight. The medium was then replaced by 50 ml OPTI-MEM, and cells were incubated in this medium for another 72 hours. The medium with the secreted S120AT121A HA-tagged mouse leptin was collected and filtered through a 0.22 µm filter, and complete (Roche Diagnostics) protease inhibitor was added.

The S120AT121A HA-tagged mouse leptin was purified on a 1 ml anti-HA affinity column (Roche diagnostics). The medium was loaded at a flow rate of 0.3 ml/min. The column was washed with 25 ml equilibration buffer (20 mM Tris/HCl, pH 7.5, 100 mM NaCl, 0.1 mM EDTA)+0.05% Tween-20, followed by 10 ml equilibration buffer without Tween-20. The S120AT121A HA-mouse leptin was eluted with HA peptide (1 mg/ml) in equilibration buffer.

Example 6

The S120AT121A Mouse Leptin Mutant does not Induce JAK-STAT Signaling of the Mouse Leptin Receptor HEK293T cells were seeded in 6 well plates at $4 \times 10^5$ cells/well and grown for 20 hours. The cells were then transfected with the pMET7-mLRlo and pXP2d2-rPAP1 plasmids, using the standard calcium phosphate precipitation technique. One day after transfection, the cells were washed with phosphate buffered saline, and cultured in DMEM medium supplemented with 10% fetal calf serum and 50 µg/ml gentamycin. Two days after transfection, the cells were dissociated with cell dissociation buffer (Invitrogen) and resuspended in 2 ml of DMEM medium supplemented with 10% fetal calf serum and 50 µg/ml gentamycin. 50 µl of the cell suspension was seeded in each well of a black 96-well plate (Costar). In each well, 50 µl of the appropriate dilution of medium containing either HA-tagged mouse leptin, R20N mouse leptin, L13N mouse leptin or S120AT121A mouse leptin was added.

The pMET7-mLRlo plasmid encodes the long form of the mouse leptin receptor, with a C-terminal myc tag. The pXP2d2-rPAP1 plasmid encodes the luciferase gene, under control of the STAT3-dependent rat pancreatitis-associated protein-1 promoter.

Incubation of the transfected HEK293T cells with wt HA-tagged mouse leptin leads to concentration-dependent luciferase activity. Incubation of the transfected HEK293T cells with the R20N mutant HA-tagged mouse leptin, the L13N mutant HA-tagged mouse leptin or the S120AT121A mouse leptin does not lead to an appreciable increase of luciferase activity in the transfected cells.

Example 7

The S120AT121A Mouse Leptin Inhibits Binding of wt Leptin to the Leptin Receptor $8 \times 10^6$ COS-1 cells were seeded in a 175 cm$^2$ flask, and grown overnight in DMEM medium supplemented with 10% fetal calf serum and 50 µg/ml gentamycin.

The cells were transfected with the pMET7-mLRCRM2-his6 using the PEI transfection method. pMET7-mLRCRM2-his6 encodes amino acids 407-604, corresponding to the CRM2 module of the murine leptin receptor, followed by a C-terminal his6 tag. After 4 hours, the medium was replaced by fresh DMEM medium supplemented with 10% fetal calf serum and 50 µg/ml gentamycin, and cells were grown overnight. The medium was then replaced by 50 ml OPTI-MEM, and cells were incubated in this medium for another 72 hours. The medium with the secreted His-tagged CRM2 leptin was collected and cells were removed by centrifugation. This medium is referred to as CRM2-his medium.

$8 \times 10^6$ COS-1 cells were seeded in a 175 cm$^2$ flask, and grown overnight in DMEM supplemented with 10% fetal calf serum and 50 µg/ml gentamycin.

The cells were transfected with the pCDM8 AP-mLep plasmid using the PEI transfection method. The pCDM8 AP-mLep plasmid allows expression of a fusion protein, consisting of murine leptin linked to the C-terminus of human secreted alkaline phosphatase (SEAP). After 4 hours, the medium was replaced by fresh DMEM medium, and cells were grown overnight. The medium was then replaced by 50 ml OPTI-MEM, and cells were incubated in this medium for another 72 hours. The medium with the secreted SEAP-leptin was collected and cells were removed by centrifugation. This medium is referred to as SEAP-leptin medium.

Figure 3:
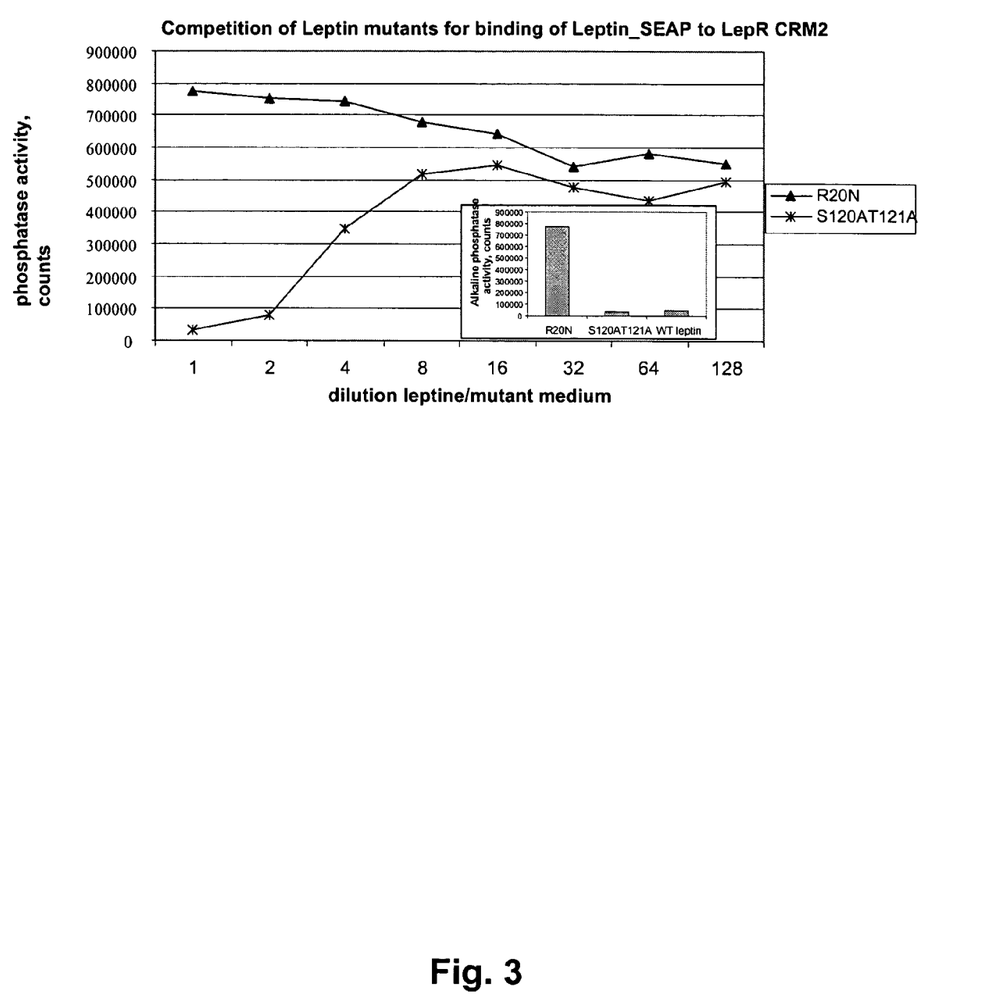
FIG. 3: Competition of Leptin mutants for binding of SEAP-Leptin to LepR CRM2. Inset: binding of SEAP-Leptin to LepR CRM2 in the presence of undiluted medium containing WT leptin or the R20N or S120AT121A mutant leptin.

Maxisorp plates (Nunc) were coated overnight at 6° C. with 0.25 µg/ml anti-His5 antibody (Qiagen). Plates were washed four times with phosphate buffered saline pH 7.5 containing 0.1% Tween 20. The free protein binding sites on the plates were blocked by incubation with 1% casein in phosphate buffered saline pH 7.5 at 37° C. for two hours. Plates were washed four times with phosphate buffered saline pH 7.5 containing 0.1% Tween 20. The plates were incubated for 2 hours at 37° C. with the undiluted medium containing the his-tagged CRM2 of the murine leptin receptor. Plates were washed four times with phosphate buffered saline pH 7.5 containing 0.1% Tween 20. The plates were then incubated with SEAP-leptin medium and different concentrations of either HA-tagged mouse leptin or S120AT121A leptin antagonist. Addition of S120AT121A mouse leptin or WT leptin, but not of mutant R20N inhibits the binding of the SEAP-leptin to the his-tagged CRM2 of the murine leptin receptor. The results are shown in FIG. 3.

Example 8

The S120AT121A Mouse Leptin Mutant Inhibits the JAK-STAT Signaling of the Mouse Leptin Receptor HEK 293T cells were seeded in 6 well plates at $4 \times 10^5$ cells/well and grown for 20 hours. The cells were then transfected with the pMET7-mLRlo and pXP2d2-rPAP1 plasmids, using the standard calcium phosphate precipitation technique. One day after transfection, the cells were washed with phosphate buffered saline, and cultured in DMEM medium supplemented with 10% fetal calf serum and 50 µg/ml gentamycin. Two days after transfection, the cells were dissociated with cell dissociation buffer (Invitrogen) and resuspended in 2 ml of DMEM medium, supplemented with 10% fetal calf serum and 50 µg/ml gentamycin. 50 µl of the cell suspension was seeded in each well of a black 96-well plate (Costar). OPTI-MEM medium, containing wt HA-tagged leptin (see, Example 4) was diluted 16 fold in OPT-MEM. 50 µl of this diluted medium was added to the cells, together with 50 µl of dilution of anti-HA purified (see Example 5) HA tagged S120AT121A leptin. The cells were then incubated overnight. The medium was removed and the cells were incubated with 50 µ of lysis buffer (25 mM Tris, pH 7.8; 2 mM EDTA; 2 mM DTT; 10% glycerol; 1% Triton X-100) for 10 minutes. 35 µl of luciferase substrate buffer (20 mM Tricine; 1.07 mM $(MgCO_3)_4Mg(OH)_2.5H_2O$; 2.67 mM $MgSO_4.7H_2O$; 0.1 mM EDTA; 33.3 mM DTT; 270 mM Coenzyme A; 470 mM Luciferin; 530 mM ATP; final pH 7.8) was then added to the lysate, and the light emission was measured in a TopCount Chemiluminescence Counter (Packard).

Figure 4:
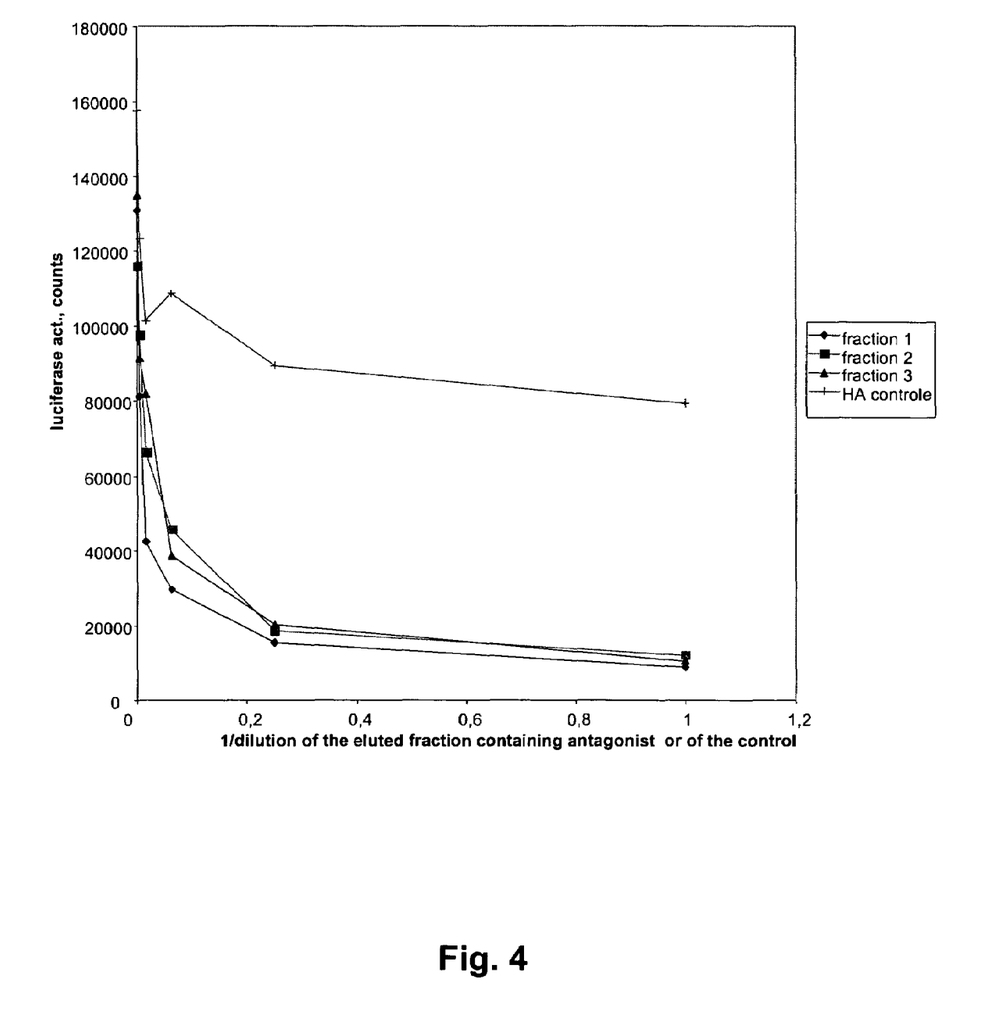
FIG. 4: Incubation of the transfected HEK293T cells with the wt HA-mouse leptin induces luciferase activity. Co-incubation with the HA-tagged S120AT121A mouse leptin, purified on the anti-HA affinity column, leads to strong inhibition of the leptin-induced luciferase activity, and the luciferase activity drops to the level of non-stimulated cells. 50 μl of the HEK293T cells were incubated with WT leptin and 50 μl of different dilutions of fractions 1 (◇),2 (□), and 3(Δ) eluted from the anti HA column with 1 mg/ml HA peptide in equilibration buffer. As a control (+), 50 μl of the HEK293T cells were incubated with WT leptin and 50 μl of different dilutions of the elution buffer (1 mg/ml HA peptide in equilibration buffer).

The results are shown in FIG. 4. Incubation of the transfected HEK293T cells with the wt HA-tagged mouse leptin induces luciferase activity. Co-incubation with the S120AT121A mutant inhibits the leptin-induced luciferase activity. This inhibitory effect is not seen with the L13N nor the R20N mutants.

REFERENCES

Barton, V. A., Hudson, K. R. and Heath, J. K. (1999) Identification of three distinct receptor binding sites of murine interleukin-11. *J. Biol. Chem.* 274, 5755-5761.

Baumann, H., Morella, K. K., White, D. W., Dembski, M., Bailon, P. S., Kim, H., Lai, C.-F. and Tartaglia, L. A. (1996) The full-length leptin receptor has signaling capabilities of interleukin 6-type cytokine receptors. *Proc. Natl. Acad. Sci.* 93, 8374-8378.

Boulanger, M. J., Chow, D.-C., Brevnova, E. E. and Garcia, K. C. (2003) Hexameric structure and assembly of the interleukin-6/IL-6 α-receptor/gp130 complex. *Science* 300, 2101-2104.

Bravo, J., and Heath, J. K. (2000) Receptor recognition by gp130 cytokines. *EMBO. J.* 19, 2399-2411.

Busso, N., So, A., Chobaz-Péclat V., Morard, C., Martinez-Soria E., Talabot-Ayer D. and Gabay C. (2002) Leptin signaling deficiency impairs humoral and cellular immune responses and attenuates experimental arthritis. *J. Immunol.* 168, 875-882.

Chow, D.-C., He, X.-L., Snow, A. L., Rose-John, S. and Garcia, K. C. (2001) Structure of an extracellular gp130 cytokine receptor signaling complex. *Science* 291, 2150-2155.

Cohen, S. L., Halaas, J. L., Friedman, J. M., Chait, B. T., Bennett, L., Chang, D., Hecht, R. and Collins, F. (1996) Human leptin characterization. *Nature* 382, 589.

Di Marco, A.; Gloaguen, I., Graziani, R., Paonessa, G., Saggio, I., Hudson, K. R., and Laufer, R. (1996) Identification of Ciliary neurotrophic factor (CNTF) residues essential for leukemia inhibitory factor receptor binding and generation of CNTF receptor antagonists. *Proc. Natl. Acad. Sci. USA* 93, 9247-9252.

Faggioni, R., Fantuzzi, G., Fuller, J., Dinarello, C. A., Feingold, K. R., Grunfeld, C. (1998) IL-1 beta mediates leptin induction during inflammation. *Am. J. Physiol.* 274, R204-208.

Fong, T. M., Huang, R.-R. C., Tota, M. R., Mao, C., Smith, T., Varnerin, J., Karpitskiy, V. V., Krause, J. E., Van Der Ploeg, L. H. T. (1998) Localization of Leptin Binding Domain in the leptin receptor. *Molecular Pharmacology* 53, 234-240.

Gainsford, T., Willson, T. A., Metcalf, D., Handman, E., McFarlane, C., Ng, A., Nicola, N. A., Alexander, W. S., Hilton, D. J. (1996) Leptin can induce proliferation, differentiation, and functional activation of hemopoietic cells. *Proc. Natl. Acad. Sci. USA* 93 14564-14568.

Ghilardi, N., Skoda, R. C. (1997) The leptin receptor activates janus kinase 2 and signals for proliferation in a factor-dependent cell line. *Mol. Endocrinol.* 11, 393-9.

Grunfeld, C., Zhao, C., Fuller, J., Pollack, A., Moser, A., Friedman, J., Feingold, K. R. (1996) Endotoxin and cytokines induce expression of leptin, the ob gene product, in hamsters. *J. Clin. Invest.* 97, 2152-2157.

Holm, L. and Sander, C. (1997) Dali/FSSP classification of three-dimensional protein folds. *Nucleic Acids Res.* 25, 231-234.

Hudson, K. R., Vernallis, A. B., and Heath J. K. (1996) Characterization of the receptor binding sites of human leukemia inhibitory factor and creation of antagonists. *J. Biol. Chem.* 271, 11971-11978.

Inoue M., Nakayam, C., Kikuchi, K., Kimura, T., Ishige, Y., Ito, A., Kanaoka, M. and Noguchi, H. (1995) D1 cap region involved in the receptor recognition and neuronal cell survival activity of human Ciliary neurotrophic factor. *Proc. Natl. Acad. Sci. USA* 92, 8579-8583.

Kalai, M.; Montero-Julian., F., Grötzinger, J.; Fontaine, V., Vandenbussche, P., Deschuyteneer, R., Wollmer, A., Brailly, F., and Content, J. (1997) Analysis of the human Interleukin-6/Human Interleukin-6 Receptor binding interface at the amino acid level: proposed mechanism of interaction. *Blood* 89 1319-1333.

Loffreda, S., Yang, S. Q., Lin, H. Z., Karp, C. L., Brengman, M. L., Wang, D. J., Klein, A. S., Bulkley, G. B., Bao, C., Noble, P. W., Lane, M. D., Diehl, A. M. (1998) Leptin regulates proinflammatory immune responses. *Faseb. J.* 12, 57-65.

Lord, G. M., Matarese, G., Howard, J. K., Baker, R. J., Bloom, S. R., Lechler, R. I. (1998) Leptin modulates the T-cell immune response and reverses starvation-induced immunosuppression. *Nature* 394, 897-901.

Matarese, G., Di Giacomo, A., Sanna, V., Lord, G. M., Howard, J. K., DiTuoro, A., Bloom, S. R., Lechler, R. I., Zappacosta, S. and Fontana, S. (2001) Requirement for leptin in the induction and progression of autoimmune encephalomyelitis. *J. Immunology,* 166, 5909-5916.

Matarese, G., Sanna, V., Lechler, R. I., Sarvetnick, N., Fontana, S., Zappacosta, S., and La Cava, A. (2002) Leptin accelerates autoimmune diabetes in female NOD mice. *Diabetes* 51, 1356-1361.

Mykoniatis A., Anton, P. M., W L K, M., Wang, C. C., Ungsunan, L., Blüher, S., Venihaki, M., simeonidis, S., Zacks, J., Zhao, D., Sougioultzis, S., Karalis, K., Mantzoros, C., and Pothoulakis, C. (2003) Leptin mediates Clostridium Difficile Toxin A-induced enteritis in mice. *Gastroenterology* 124, 683-691.

Sanna, V., Di Giacomo, A., La Cava, A., Lechler, R. I., Fontana, S., Zappacosta, S., and Matarese, G. (2003) Leptin surge precedes onset of autoimmune encephalomyelitis and correlates with development of pathogenic T cell responses. *J. Clin. Invest.* 111, 241-250.

Savino, R., Lahm, A., Giogio, M., Cabibbo, A., Tramontano, A. and Ciliberto, G. (1993) Saturation mutagenesis of the human interleukin 6 receptor-binding site: Implications for its three-dimensional structure. *Proc. Natl. Acad. Sci. USA* 90, 4067-4071.

Siegmund, B., Lehr, H. A., and Fantuzzi, G. (2002) Leptin: A pivotal mediator of intestinal inflammation in mice. *Gastroenterology* 122, 2011-2025.

Sierra-Honigmann, M. R., Nath, A. K., Murakami, C., García-Cardeña, G., Papapetropoulos, A., Sessa, W. C., Madge, L. A., Schechner, J. S., Scwabb, M. B., Polverini, P. J., Flores-Riveros, J. R. (1998) Biological action of leptin as an angiogenic factor. *Science* 281, 1683-1686.

Zhang, F., Basinski, M. B., Beals, J. M., Briggs, S. L., Churgay, L. M., Clawson, D. K., DiMarchi, R. D., Furman, T. C., Hale, J. E., Hsiung, H. M., Schoner, B. E., Smith, D. P., Zhang, X. Y., Wery, J. P., Schevitz, R. W. (1997) Crystal structure of the obese protein leptin-E100. *Nature* 387, 206-209.

What is claimed is:

1. An isolated peptide comprising SEQ ID NO:1, said peptide having leptin antagonist activity.

2. A pharmaceutical composition for use in a subject, the pharmaceutical composition comprising: a peptide comprising SEQ ID NO:1, said peptide having leptin antagonist activity presented in a form suitable for administration to a subject.

* * * * *

UNITED STATES PATENT AND TRADEMARK OFFICE
CERTIFICATE OF CORRECTION

PATENT NO. : 7,423,113 B2 Page 1 of 1
APPLICATION NO. : 10/926798
DATED : September 9, 2008
INVENTOR(S) : Jan Tavernier and Frank Peelman

It is certified that error appears in the above-identified patent and that said Letters Patent is hereby corrected as shown below:

On the Title page
ITEM (56) References Cited, 2$^{nd}$ Column,
   OTHER PUBLICATIONS,
          Line 17,    change "(ob-Rb)" to --(Ob-Rb)--

COLUMN 3,   Line 21,   change "do not -affect" to --do not affect--

Signed and Sealed this

Sixteenth Day of November, 2010

David J. Kappos
*Director of the United States Patent and Trademark Office*